United States Patent
Wake et al.

(10) Patent No.: US 6,331,700 B1
(45) Date of Patent: Dec. 18, 2001

(54) DETECTOR ARRAY VARIABLE GAIN AMPLIFIERS FOR USE IN A LASER IMAGING APPARATUS

(75) Inventors: Robert H. Wake, Sunrise; Richard J. Grable, Plantation, both of FL (US); Sastry L. A. Kasibhatla, University Heights, OH (US)

(73) Assignee: Imaging Diagnostic Systems, Inc., Plantation, FL (US)

(*) Notice: Subject to any disclaimer, the term of this patent is extended or adjusted under 35 U.S.C. 154(b) by 0 days.

(21) Appl. No.: 09/712,244

(22) Filed: Nov. 15, 2000

Related U.S. Application Data

(62) Division of application No. 08/979,328, filed on Nov. 26, 1997, now Pat. No. 6,150,649.
(60) Provisional application No. 60/032,590, filed on Nov. 29, 1996, provisional application No. 60/032,591, filed on Nov. 29, 1996, provisional application No. 60/032,592, filed on Nov. 29, 1996, provisional application No. 60/032,593, filed on Nov. 29, 1996, and provisional application No. 60/032,594, filed on Nov. 29, 1996.

(51) Int. Cl.$^7$ ............................ H03G 3/30; H01N 1/04
(52) U.S. Cl. ........................ 250/208.1; 250/214 A; 250/214 AG; 600/476
(58) Field of Search ............ 250/214 R, 214 A, 250/214 AG, 214.1, 208.1, 208.2, 332, 334, 341.1; 356/218, 222, 224; 330/278, 279, 280, 281; 600/476, 477, 475, 473, 407

(56) References Cited

U.S. PATENT DOCUMENTS

| | | |
|---|---|---|
| 3,863,154 | 1/1975 | Marwell et al. . |
| 4,499,430 | 2/1985 | Fujii . |
| 4,554,460 | 11/1985 | Klein . |
| 5,408,093 | 4/1995 | Ito et al. . |
| 5,471,049 | 11/1995 | Cain . |
| 5,477,051 | 12/1995 | Tsuchiya . |
| 5,572,118 | 11/1996 | Lewis . |
| 5,692,511 | 12/1997 | Grable . |
| 5,708,414 | 1/1998 | Peltier et al. . |
| 5,717,608 | 2/1998 | Jensen . |
| 5,719,398 | 2/1998 | Colak . |
| 5,815,410 | 9/1998 | Heinke et al. . |
| 5,880,827 | 3/1999 | Heinke . |
| 6,031,217 * | 2/2000 | Aswell et al. ............ 250/208.1 |
| 6,097,021 * | 8/2000 | Aswell et al. ............ 250/208.1 |
| 6,150,649 * | 11/2000 | Wake et al. ............. 250/208.1 |
| 6,218,673 * | 4/2001 | Gore et al. ............. 250/474.1 |

* cited by examiner

*Primary Examiner*—John R. Lee
(74) *Attorney, Agent, or Firm*—Shlesinger, Arkwright & Garvey LLP

(57) ABSTRACT

A detector array for a laser imaging apparatus comprises a plurality of detectors disposed in an arc around an opening in which an object to be scanned is disposed; and a variable gain integrator operably connected to each detector to accommodate the dynamic range of each detector. A method for collecting data for use in image reconstruction of an object being scanned is also disclosed, comprising the steps of providing a plurality of detectors disposed in an arc around the object to be scanned, including a variable gain amplifier connected to each detector; impinging a laser beam at a point on the object; integrating the input to each integrating amplifier at several time intervals; recording each output at each integration interval for use in image reconstruction; orbiting the detectors and the laser beam to a next point on a circle; and repeating steps until a complete circle has been traversed.

3 Claims, 4 Drawing Sheets

DETECTOR ARRAY VARIABLE GAIN AMPLIFIERS FOR USE IN A LASER IMAGING APPARATUS

RELATED APPLICATION

This application is a division of Nonprovisional application Ser. No. 08/979,328, filed Nov. 26, 1997, now U.S. Pat. No. 6,150,649, and which is based on provisional application Serial No. 60/032,590 filed Nov. 29, 1996, which is hereby incorporated by reference.

This application is also related to copending applications filed on Nov. 4, 1997, entitled "Detector Array for Use in Laser Imaging Apparatus," claiming priority based on provisional applications serial Nos. 60/032,591, 60/032,592, and 60/032,593 filed on Nov. 29, 1996, which are all hereby incorporated by reference.

This application is also related to provisional application Serial No. 60/032,594, filed Nov. 29, 1996, which is hereby incorporated by reference.

This application is also related to application Ser. No. 08/484,904, filed Jun. 7, 1995, now U.S. Pat. No. 5,692,511, which is hereby incorporated by reference.

FIELD OF THE INVENTION

The present invention relates generally to a diagnostic medical imaging apparatus that employs a near-infrared laser as a radiation source and more particularly to a detector array with variable gain amplifiers to accommodate the wide dynamic range of signal available from the detector.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present graphic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in graphic mammograms 2–3 cm dimensions are required. Calcium deposits used for inferential detection of tumors in conventional mammography also appear to be associated with tumors of large size. For these reasons, graphic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested, as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This technique is called optical imaging. Optical imaging and spectroscopy are key components of optical tomography. Rapid progress over the past decade have brought optical tomography to the brink of clinical usefulness. Optical wavelengths do not penetrate in vivo tissue in a straight line as do x-rays. This phenomena causes the lights to scatter inside the tissue before they emerge out of the scanned sample.

Because x-ray propagation is essentially straight-line, relatively straight forward techniques based on the Radon transform have been devised to produce computed tomography images through use of computer algorithms Multiple measurements are made through 360° around the scanned object. These measurements, known as projections, are used to back-project the data to create an image representative of the interior of the scanned object.

In optical tomography, mathematical formulas and projection techniques have been devised to perform a reconstruction function somewhat similar to x-ray tomography. Acquiring data through optical measurements of the photons emerging from a scanned object is the first step in the imaging process. Light photon propagation through in vivo breast tissue results in high attenuation of the beam intensity. Methods for detection of low light levels and preserving a wide dynamic measurement range are essential components of a practical computed tomography laser scanner for the breast and other soft tissues. These sophisticated detection techniques are required to acquire the data necessary for meaningful image reconstructions.

OBJECTS AND SUMMARY OF THE INVENTION

It is an object of the present invention to provide a detector array that can detect the significantly different light levels emerging from a scanned object.

It is another object of the present invention to provide a processing circuit for a detector that can accommodate the dynamic range of the detector.

It is still another object of the present invention to provide a detector with a variable gain amplifier to accommodate the dynamic range of the detector, from approximately $50 \times 10^{-12}$ A to $50 \times 10^{-6}$ A.

It is another object of the present invention to a detector with an amplifier with variable integration time to accommodate the dynamic range of the detector.

In summary, the present invention provides a detector array for a laser imaging apparatus comprising a plurality of detectors disposed in an arc around an opening in which an object to be scanned is disposed; and a variable gain integrator operably connected to each detector to accommodate the dynamic range of each detector.

A method for collecting data for use in image reconstruction of an object being scanned is also disclosed, comprising the steps of providing a plurality of detectors disposed in an arc around the object to be scanned, including a variable gain amplifier connected to each detector; impinging a laser beam at a point on the object; integrating the input to each integrating amplifier at several time intervals; recording each output at each integration interval for use in image reconstruction; orbiting the detectors and the laser beam to a next point on a circle; and repeating steps until a complete circle has been traversed.

These and other objects of the present invention will become apparent from the following detailed description.

BRIEF DESCRIPTIONS OF THE DRAWINGS

DETAILED DESCRIPTION OF THE INVENTION

Figure 1:
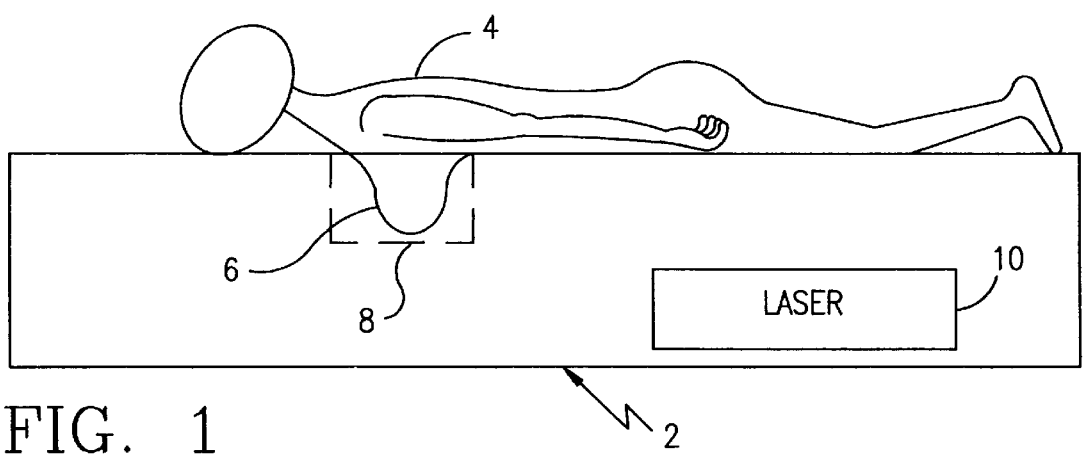
FIG. 1 is a schematic side elevational view of a laser imaging apparatus with a patient in a prone position with one of her breasts positioned within a scanning chamber for an optical tomographic study.

A scanning apparatus 2, such as that described in copending application Ser. No. 08/484,904, filed Jun. 7, 1995, is schematically disclosed in FIG. 1. A patient 4 is positioned prone on a top surface of the apparatus 2 with her breast 6 disposed pendent within a scanning chamber 8. A laser beam from a laser source 10 is brought to the scanning chamber 8 to illuminate the breast 6.

The scanning chamber 8 comprises of an array of detectors 12 disposed around the breast in an arc. A laser beam 14 is brought into the scanning chamber to impinge on the breast 6. A laser beam traversing through the breast 6 and exiting at the other side, as generally disclosed at 16, 18, or 20 is picked up by the respective detectors 12. The laser beam 14 and the array of detectors 12 are moved in an orbit 17 around the breast 6 at equally spaced angular positions until a complete circle has been traversed. At each angular position, light detected by the array of detectors 12 is recorded for later use in reconstructing an image of the breast 6. Each detector 12 includes a device to restrict its field of view to a small patch of surface of object being scanned, as disclosed in copending application filed Nov. 4, 1997, claiming priority based on provisional application serial No. 60/032,591, filed Nov. 29, 1996, both of which are hereby incorporated by reference.

The laser source 14, preferably a near-inferred laser, illuminates the breast 6 and each detector sees light that is transmitted through a portion of the breast and remitted, such as for detectors 12 at positions A, B and C, for which light paths 18, 16 and 20 are shown. Each detector has a restricted field of view whose axis is generally indicated at 22. The light level that the detectors see are generally quite low and varied with detector position and scanned object size and composition. Between the detector at position A and the detector at position B, the light level can differ by a factor of $10^3$ to $10^5$. This is due to light absorption within the scanned object and the difference in the path lengths 18 and 16. The light transmission is given by:

$$I = I_0 e^{-\mu x} \quad (1)$$

where I is the detected intensity, $I_0$ is the incident intensity, $\mu$ is the linear attenuation co-efficient of the medium and x is the path length in the medium. The ratios of intensities detected by the detectors at positions A and B is given by:

$$R = e^{-\mu(x_b - x_a)} \quad (2)$$

where R is the ratio of intensities, $x_a$ is path length in the medium for detector at position A and $x_b$ is the path length in the medium for the detector at position B. For a $\mu$ of 1.0 $cm^{-1}$, which is a typical value for tissue and path lengths of xa=2 cm and xb=11 cm, the intensity ratio between these detectors is 8103:1.

Different scanned objects, and different breasts can exhibit attenuation ranges of 10:1 or greater. The net effect is that the detectors are required to measure light intensities over a range of $10^6$:1 in the worst case.

The detector 12 is preferably a silicone photodiode, which advantageously comes in small physical size and exhibits insensitivity to acceleration and magnetic fields, unlike photomultiplier tubes. The quantum efficiency of diodes is far better than that of photomultiplier tubes at the 800 nm near-inferred wavelength of biological interest. Photodiodes are available with extremely small leakage currents for conductive application and high shunt resistances for photovoltaic application. In the scanning application of the present invention, the photodiode currents are as low as 50 pA ($50 \times 10^{-12}$ A).

Figure 3:
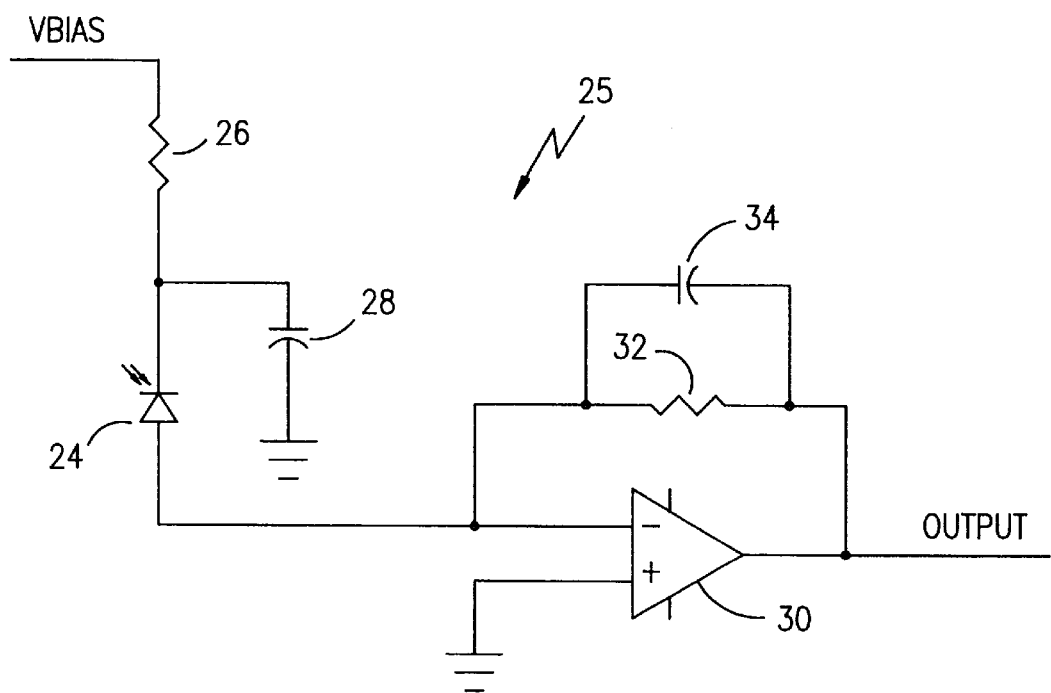
FIG. 3 is a schematic diagram of a transimpedence amplifier for processing the output of a detector.

A transimpedence amplifier 25 for a photodiode is shown in FIG. 3. The photodiode 24 is reverse biased by the positive VBIAS voltage applied to resistor 26. The capacitor 28 serves to remove any noise from the VBIAS supply which would otherwise contaminate the output signal. The photocurrent from the photodiode 24 is impressed on the inverting input of an operational amplifier 30. This causes the inverting input's voltage to rise, causing the operational amplifier's output to swing negative until the photocurrent is matched by the current through the feedback resistor 32. Capacitor 34 serves to remove high frequency noise and to stabilize the operational amplifier 30. The gain of the transimpedence amplifier is the value of the resistor 32.

The value of the resistor 32 is chosen so as to not saturate the operational amplifier 30 with the largest input signal. A maximum input current of 50 $\mu$A produces a 10 V signal across a resistor of 200 k$\Omega$. The minimum input signal is 50 pA which produces a 10 $\mu$V output signal from the operational amplifier 30. A signal this low is very difficult to handle. Even the best low-input-current operational amplifiers have input offsets of hundreds of microvolts, larger than the signal. Precision operational amplifiers are available which exhibit input offset voltages below 10 microvolts. However, they also exhibit input bias currents of a nanoamp or more, many times the 50 pA being measured.

Processing a 10 micro volt signal is very difficult. An analog-to-digital converter (ADC) would need more than 20-bits of resolution to digitize this signal and the 10 volt maximum signal. Such ADCs are much slower than the 0.5–1 MHz digitization rate requirement of the scanning application in the present invention.

Figure 4:
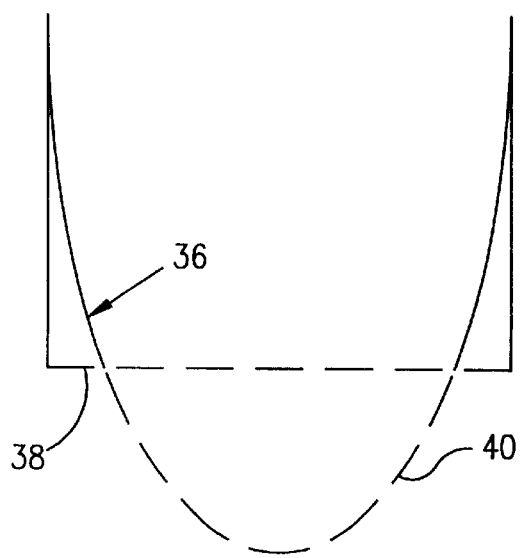
FIG. 4 is a response curve of a detector array where part of the curve is below the threshold minimum value of the processing circuit.

The lack of sensitivity for the circuit 25 is illustrated in a response curve 36 for the detector array from the output of the amplifier circuit, as best shown in FIG. 4. Taking the x-axis as the detector positions in the array, and the y-axis as the magnitude of the output of each detector, it will be seen that the amplifier circuit is not sensitive enough for those detectors located farther away the laser beam 14. Light arriving at the farther detectors provide an output at the same level as the minimum threshold value 38 of the circuit, which is undesirable. The response curve, including the portion 40 indicated in broken line, must be above the minimum threshold value 38 of the circuit to be useful in image reconstruction.

Figure 5:
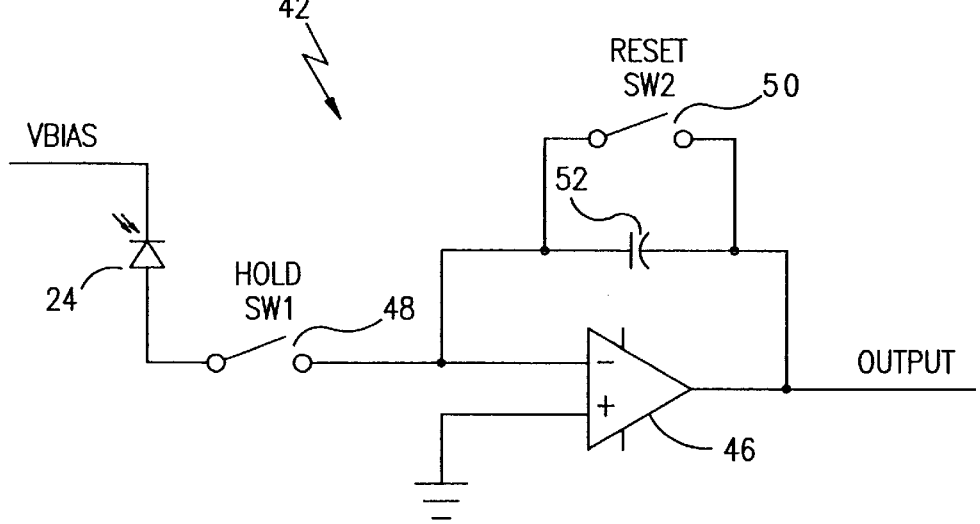
FIG. 5 is a schematic diagram of a switched integrator used in the present invention.

To alleviate the above problem, a switched integrator circuit 42 is used to increase the dynamic range of the amplifier circuit 25. Referring to FIG. 5, current from photodiode 24 is integrated by a switched integrator 42 whose integration time is varied to accommodate the dynamic range of the detectors. The photocurrent from the photodiode 24 is impressed on the inverting input of operational amplifier 46 if switch 48, the "HOLD" switch is closed. If switch 50, the "RESET" switch is open, the output of the operational amplifier 46 ramps negative, charging capacitor 52 at a rate given by:

$$V=(i*t)/C \quad (3)$$

where V is the output voltage, i is the current, t is the time that the current has been charging the capacitor 52 and C is the value of the capacitor 52. Analogous to the transimpedence amplifier 25, the gain of the switched integrator 42 is given by t/C. Thus, the gain can be set by changing the capacitor or by changing the integration time. In the present invention, the integration time is varied to adjust the gain of the circuit 42 for the wide variation of signal amplitude encountered by the detectors.

Figure 6:
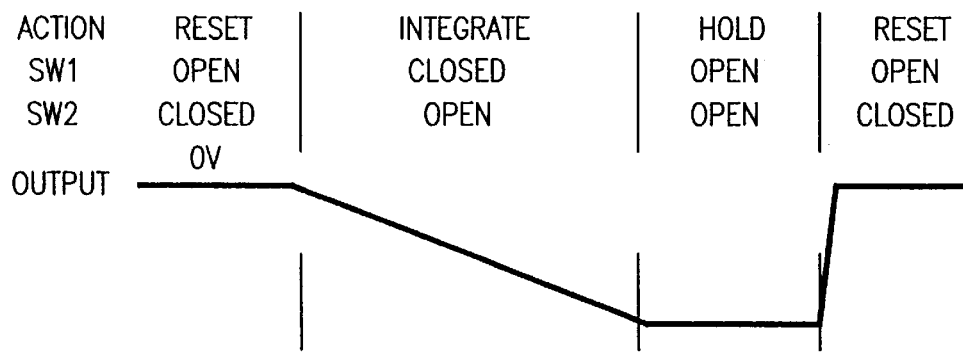
FIG. 6 is a sequence of functions of the switched integrator of FIG. 5.

The function of the switches and the resulting output voltage are illustrated in FIG. 6. Closing the reset switch 50 causes the output level to go to zero. This is done immediately prior to making a measurement. Opening the reset switch 50 and closing the hold switch 48 causes the integrator to integrate the input current. Opening the hold switch 48 causes the output voltage level to stop at its current value. This is done whenever the signal level is to be digitized. Closing the reset switch 50 again resets the output back to zero preparatory to making another measurement.

In the present invention, there is one switched integrator 42 for each of a plurality of photodiodes 24, and each measurement point along the orbit will consist of several different integration times, thereby accommodating a wide variation in photocurrents.

Figure 7:
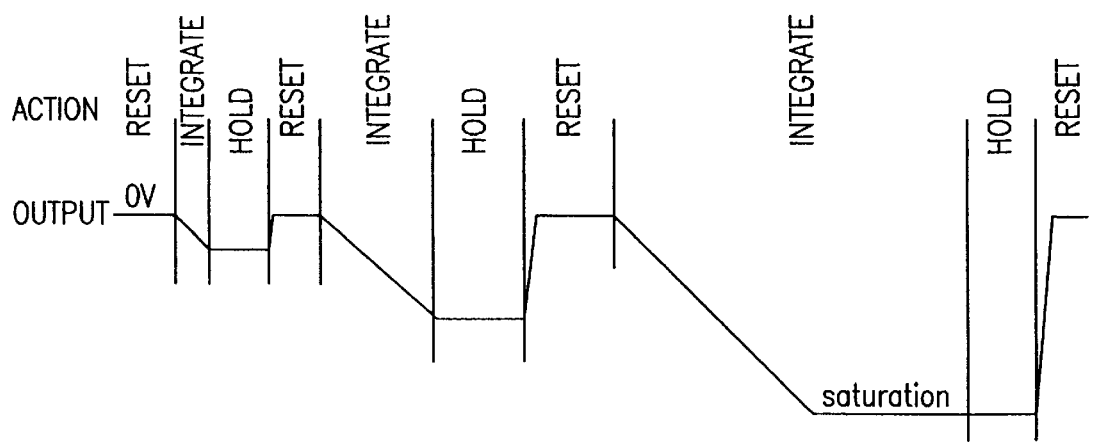
FIG. 7 is a sequence of functions of the switched integrator of FIG. 5 with successively longer integration times.

Referring to FIG. 7, the switched integrator behavior for three different integration intervals, each successively longer is illustrated. The third integration interval is sufficiently long that operational amplifier saturates, which is harmless. The integration times are preferably chosen in the range 2 $\mu$s–128 ms.

Figure 8:
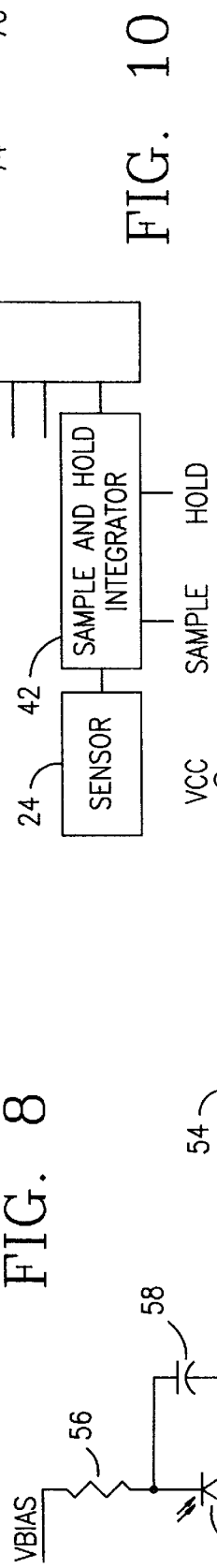
FIG. 8 is a composite response curve for a detector array obtained from three response curves of differing integration times.

A composite response curve 49 is generated from three integration times, as best shown in FIG. 8. Curve portion 51 is taken from a response curve of a first integration time, curve portion 53 from a response curve of a second integration time, and curve portion 55 from a response curve of a third integration time. It will be seen that the curve 49 is some distance above the minimum threshold value of the circuit 42, thereby accommodating the dynamic range of the detectors.

Figure 9:
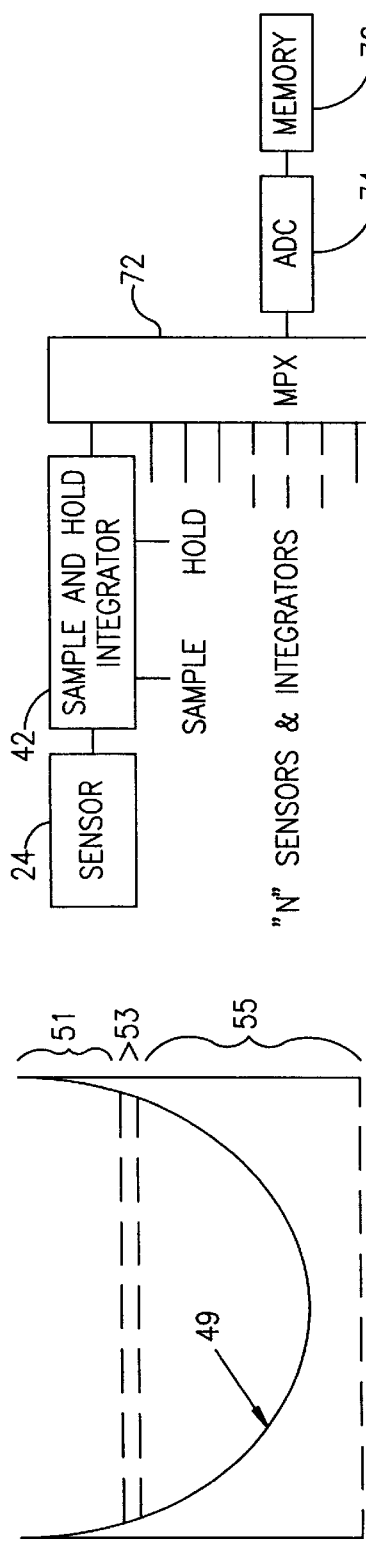
FIG. 9 is a schematic diagram of an integrating amplifier used in the present invention.

The circuit 42 is preferably implemented with a switched integrator 54 available from Burr-Brown Corporation, Tucson, Ariz., Model No. ACF2101, as best shown in FIG. 9. Only one half is shown used in the figure for clarity. The diode 24, biased by resistor 56 and capacitor 58, is applied to the operational amplifier 54 through resistor 60. Clamping diode 62 along with resistor 60 serve to limit current into the operational amplifier 54 in the event that a very large amount of light falls on the diode 24, such as the unattenuated laser.

The differential output of the operational amplifier 54 is converted to a signal-ended output signal via the commonly-used differential amplifier comprising of operational amplifiers 64, 66 and 68.

Figure 2:
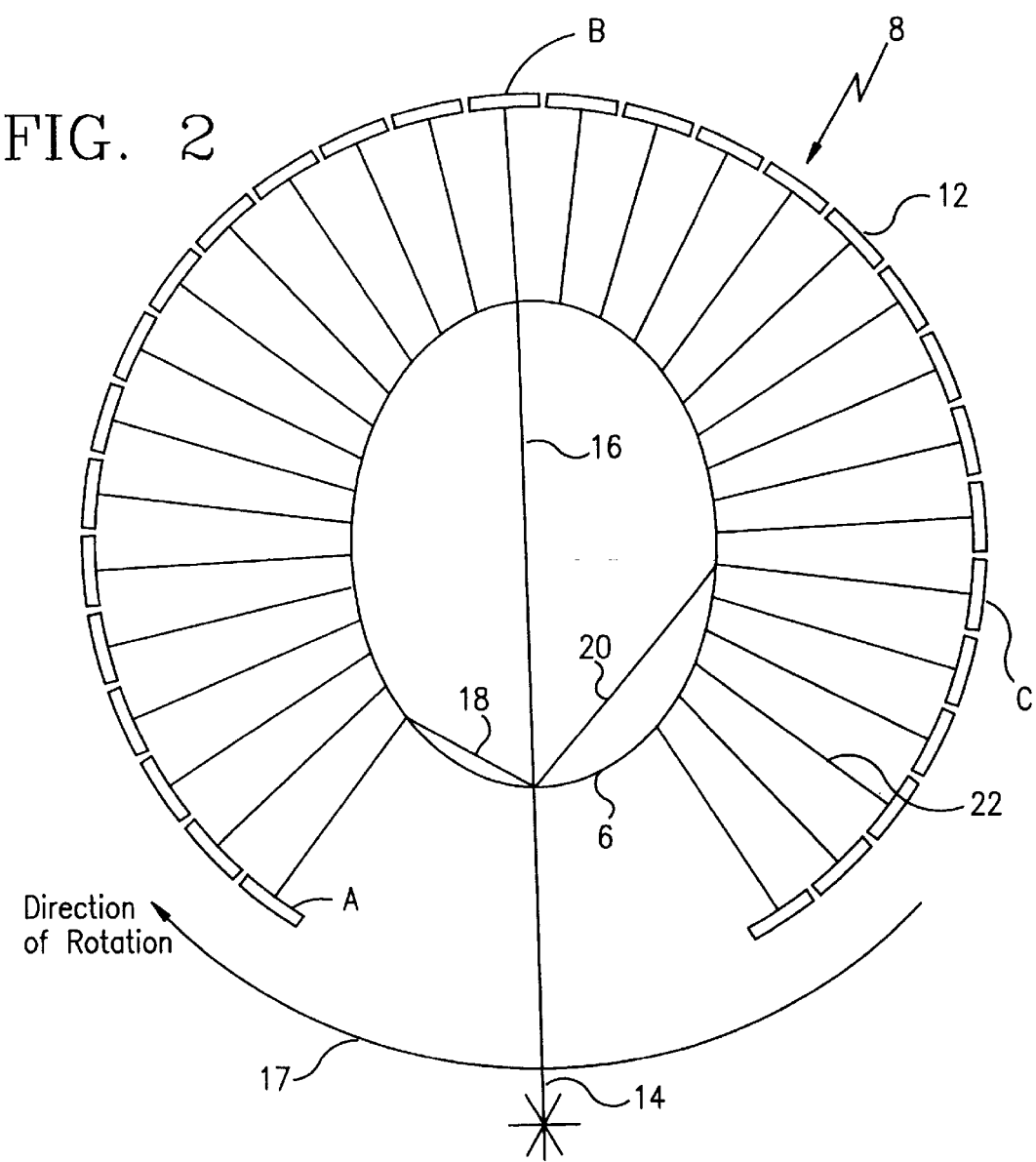
FIG. 2 is a schematic plan view of the scanning chamber in FIG. 1, showing the breast disposed within an arc of detectors.

The operational amplifier 54 has an internal 100 pF feedback capacitor (capacitor 52 in FIG. 5). With a 100 ms integration interval, the 50 pA minimum current produces an output signal of 50 mV. With the transimpedence amplifier circuit 25 (see FIG. 2), a feedback resistor of 1×10$^9$ Ω would be required for the same gain. With a 10 $\mu$s integration interval, the 50 $\mu$A maximum current produces an output signal of 5 V, within the output range of the device.

An external state machine 70 controls the timing of the HOLD and RESET inputs to the operational amplifier 54 to effect this varied integration timings. The machine 70 could be implemented in a variety of commonly known methods, such as a microprocessor.

The integration times could be fixed for the entire detector array or could be different for each detector. The integration times could be several fixed values or it could be adaptive to the light levels present.

Although diodes are preferable, the present invention also applies equally well to multipliers, avalanche diodes or any other detector with a current output.

There is typically one or more reference detectors used to measure fluctuations in the intensity of the light source. The reference detectors would be also integrated with variable intervals.

Figure 10:
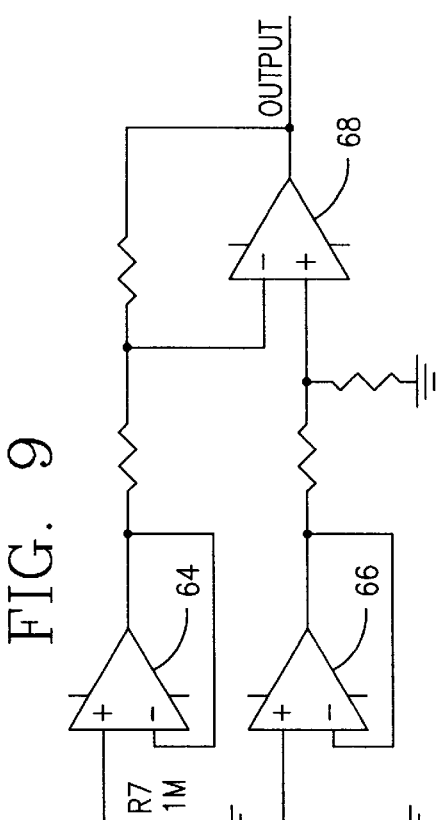
FIG. 10 is block diagram of a circuit used in the present invention to acquire data simultaneously from the detector array.

Each detector or sensor 12 is operably connected to its respective integrator 42, as best shown in FIG. 10. A multiplexer 72 is used to connect the respective integrator outputs to an analog-to-digital converter 74. The digitized individual detector or sensor response is stored in memory 76 for later use in image reconstruction. The circuit allows for simultaneous acquisition of data from all the detectors 12.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A method for collecting data for use in image reconstruction of an object being scanned, comprising the steps of:
    a) providing a plurality of detectors disposed in an arc around the object to be scanned;
    b) connecting an integrating amplifier to each detector;
    c) impinging a laser beam at a point on the object;
    d) integrating the input to each integrating amplifier at several time intervals;
    e) recording each output at each integration interval for use in image reconstruction;
    f) orbiting the detectors and the laser beam to another point on a circle; and g) repeating steps (c)–(f) until a complete circle has been traversed.

2. The method of claim 1, wherein:

a) the output of the detectors nearer to the point of impingement of the laser beam is integrated at one time interval; and b) the output of the detectors farther away from the laser beam point of impingement is integrated at a longer time interval.

3. A method for obtaining data from a photodetector array used in image reconstruction where the light intensity ratio from one photodetector to another varies substantially in the order of magnitudes, comprising the steps of:

a) integrating the output of each photodetector in the array for at least two time intervals, each time interval being longer than the previous time interval; and b) selecting the value of the integration derived from the longest time interval for those detectors receiving the smallest light signals.

* * * * *